(12) United States Patent
Padmanabha et al.

(10) Patent No.: US 11,678,834 B2
(45) Date of Patent: Jun. 20, 2023

(54) SYSTEM AND METHOD FOR NEUROPATHY DIAGNOSIS WITH WIRELESS FEEDBACK MECHANISM

(71) Applicant: Vinayaka Nandalike Padmanabha, Bengaluru (IN)

(72) Inventors: Vinayaka Nandalike Padmanabha, Bengaluru (IN); Ram Mohan Rao, Bangalore (IN); Kalburgi Narayanasa Maruthy, Bangalore (IN); Sanjay Seetharama Sharma, Bangalore (IN); Arunkumar Venkatesan, Chennai (IN)

(73) Assignee: YOSTRA LABS PRIVATE LIMITED, Bengaluru (IN)

( * ) Notice: Subject to any disclaimer, the term of this patent is extended or adjusted under 35 U.S.C. 154(b) by 1220 days.

(21) Appl. No.: 16/310,184

(22) PCT Filed: Jun. 16, 2017

(86) PCT No.: PCT/IN2017/050241
§ 371 (c)(1),
(2) Date: Dec. 14, 2018

(87) PCT Pub. No.: WO2017/216812
PCT Pub. Date: Dec. 21, 2017

(65) Prior Publication Data
US 2019/0320967 A1   Oct. 24, 2019

(30) Foreign Application Priority Data
Jun. 17, 2016 (IN) .............................. 201641020791

(51) Int. Cl.
*A61B 5/00* (2006.01)
*A61B 5/01* (2006.01)
(Continued)

(52) U.S. Cl.
CPC .......... *A61B 5/4076* (2013.01); *A61B 5/0004* (2013.01); *A61B 5/0051* (2013.01);
(Continued)

(58) Field of Classification Search
CPC ... A61B 5/0048; A61B 5/0051; A61B 5/0053; A61B 5/01; A61B 5/4824; A61B 5/4827;
(Continued)

(56) References Cited

U.S. PATENT DOCUMENTS 6,267,733 B1 * 7/2001 Peterson ............... A61B 5/4827
600/595
6,659,964 B2 * 12/2003 Lipman .................. A61B 5/483
600/557
(Continued)

*Primary Examiner* — David J. McCrosky
(74) *Attorney, Agent, or Firm* — Barry Choobin; Patent 360 LLC

(57) ABSTRACT

The various embodiments herein disclose a method and a system with a portable handheld diagnostic device for detecting and/or monitoring the prognosis of nerve impairment or diabetic peripheral neuropathy. The system provides a multi-parameter diabetic neuropathy-screening device to perform a combination of tactile threshold test, vibration threshold test, thermal threshold test and contactless skin-temperature measurement. The present invention provides a smartphone application that helps a user to operate/control the device, store and share the results. The smartphone application interacts with the hardware modules in the device and guides the user to perform the various tests. Further, the neuropathy diagnostic system provides a wireless feedback button that enables the subject to respond to various sensations during the course of the test.

12 Claims, 15 Drawing Sheets

(51) Int. Cl.
  *A61F 7/00* (2006.01)
  *A61F 7/02* (2006.01)
  *G01K 13/20* (2021.01)
(52) U.S. Cl.
  CPC .............. *A61B 5/0053* (2013.01); *A61B 5/01* (2013.01); *A61B 5/4029* (2013.01); *A61B 5/483* (2013.01); *A61B 5/6829* (2013.01); *A61B 5/7435* (2013.01); *A61F 7/007* (2013.01); *A61B 5/4842* (2013.01); *A61B 2560/0431* (2013.01); *A61B 2562/0252* (2013.01); *A61B 2562/0271* (2013.01); *A61F 2007/0075* (2013.01); *A61F 2007/0295* (2013.01); *G01K 13/20* (2021.01)
(58) Field of Classification Search
  CPC ......... A61B 5/483; A61B 5/441; A61B 5/442; A61B 2562/0252
  See application file for complete search history.

(56) References Cited

U.S. PATENT DOCUMENTS

| | | | | |
|---|---|---|---|---|
| 8,468,874 B2* | 6/2013 | Komninos | ............ | G01J 5/0265 73/40 |
| 8,579,830 B2* | 11/2013 | Golosarsky | ............ | A61B 5/483 600/557 |

* cited by examiner

SYSTEM AND METHOD FOR NEUROPATHY DIAGNOSIS WITH WIRELESS FEEDBACK MECHANISM

CROSS-REFERENCE TO RELATED APPLICATIONS

This Patent Application is a National Phase Application corresponding to the PCT Application No. PCT/IN2017/050241 filed on Jun. 16, 2017 with the title "A SYSTEM AND METHOD FOR NEUROPATHY DIAGNOSIS WITH WIRELESS FEEDBACK MECHANISM". This Patent Application claims the priority of the Indian Provisional Patent Application No. 201641020791 filed on Jun. 17, 2016 with the title "A SYSTEM AND METHOD FOR NEUROPATHY DIAGNOSIS WITH WIRELESS FEEDBACK MECHANISM", the contents of which is included herein by the way of reference.

BACKGROUND

Technical Field

The embodiments herein are generally related to a portable handheld neuropathy-diagnostic device. The embodiments herein are particularly related to a diagnostic device for performing a combination of tactile threshold test, vibration threshold test, thermal threshold test and skin temperature measurement. The embodiments herein are more particularly related to a neuropathy-diagnostic device provided with a feedback mechanism and accessed through a external computing device.

Description of the Related Art

Diabetes is a very common disease that often leads to painful neuropathy. Symptomatic diabetic neuropathy is preceded by an asymptomatic phase during which nerve conduction by the large fibers is impaired, leading to an impairment of vibration perception. Vibration threshold is the most valid measure of nerve function in diabetic patients. A decrease in vibration perception indicates neuropathy. Further, there is a decrease in thermal sensation threshold of the subject, which indicates the presence of Diabetic Peripheral Neuropathy (DPN).

Typically, vibration threshold testing includes two probes kept in contact with a patient's fingers or toes. Further, the probes are configured to apply different levels of vibration on fingers or toes and response of the patient to the vibration is determined. However, these tests do not yield comprehensive and accurate results.

The currently existing neuropathy-detecting devices are configured to perform individual tests that includes any one of tactile threshold, vibration threshold, or thermal response tests. The existing devices are bulky, not portable and need an external computing device to analyze the results. Further, the existing devices are expensive to manufacture, and is further operated only by trained health care professionals and not by individuals.

Another prior art discloses a method of screening neuropathy using a monofilament that exerts a force of ten grams at various points on the foot. If the patient is unable to determine the touch beyond ten gram, then the patient is diagnosed with DPN. However, the test disclosed in the prior art is manual, subjective, and error prone. Therefore, we need a quantified, automatic measurement of tactile threshold to overcome the disadvantages.

Hence, there is a need for a portable handheld diagnostic device for detecting and/or monitoring the prognosis of diabetic peripheral neuropathy in a subject. Further, there is a need for a system for performing a combination of tactile test, vibration test, thermal response test and skin-temperature measurement. Still further, there is a need for a system with a wireless feedback button to record the subject's feedback. Yet further, there is a need for a system for detecting and/or monitoring diabetic peripheral neuropathy and controlled by a mobile application.

The abovementioned shortcomings, disadvantages and problems are addressed herein and which will be understood by reading and studying the following specification.

OBJECT OF THE EMBODIMENTS HEREIN

The primary object of the embodiments herein is to provide a system and a method with a portable handheld diagnostic device for detecting and/or monitoring nerve impairment or diabetic peripheral neuropathy.

Another object of the embodiments herein is to provide a multi-parameter diabetic neuropathy diagnostic device and a method to perform a combination of tactile threshold test, vibration threshold test, thermal threshold response test or contactless skin temperature test.

Yet another object of the embodiments herein is to provide a neuropathy diagnostic system with a smartphone based control of all the tests.

Yet another object of the embodiments herein is to provide neuropathy diagnostic system with a wireless feedback mechanism such as feedback button for receiving a feedback from a subject during test.

Yet another object of the embodiments herein is to provide a neuropathy diagnostic device that allows a health care professional to perform simple and quick, yet accurate test to determine neuropathy in a subject.

Yet another object of the embodiments herein is to provide a neuropathy-screening device to provide instant results that are printed and further shared with other professionals.

Yet another object of the embodiments herein is to provide a neuropathy-screening device that is easily operated and manufactured at an economical cost, and is further transported easily and conveniently.

Yet another object of the embodiments herein is to provide a neuropathy-screening device for use by a person for self-diagnostic or self-evaluation purposes for detecting and/or monitoring neuropathy.

Yet another object of the embodiments herein is to provide a neuropathy-screening device which can inform the operator whether the subject is positive or negative for diabetic peripheral neuropathy.

These and other objects and advantages of the embodiments herein will become readily apparent from the following summary and the detailed description taken in conjunction with the accompanying drawings.

SUMMARY

The following details present a simplified summary of the embodiments herein to provide a basic understanding of the several aspects of the embodiments herein. This summary is not an extensive overview of the embodiments herein. It is not intended to identify key/critical elements of the embodiments herein or to delineate the scope of the embodiments herein. Its sole purpose is to present the concepts of the embodiments herein in a simplified form as a prelude to the more detailed description that is presented later.

The other objects and advantages of the embodiments herein will become readily apparent from the following description taken in conjunction with the accompanying drawings.

The various embodiments herein disclose a system with a portable handheld diagnostic device for detecting and/or monitoring nerve impairment or diabetic peripheral neuropathy in a subject. The system provides a multi-parameter diagnostic device, and performs a combination of tactile threshold test, vibration threshold test, thermal threshold test or contactless skin temperature measurement. The system includes a wireless feedback button to record a feedback of the subject. A mobile application is provided on a smartphone to control an operation of the device and display the test results. The application is run to guide a user to perform the test and store or print or transfer test report over a communication network. The usage of the invention is not limited to diagnosis of Diabetic Peripheral Neuropathy, but also to the diagnosis of Fibromyalgia, Complex Regional Pain Syndrome, Lower back pain diagnosis, Erectile Dysfunction, and Large Fiber Impairment Diagnosis. Further, the diagnostic device is applicable for human and veterinary diagnostics. Further, the test points are not limited to the feet and can be on any part of the body.

According to one embodiment herein, the system includes a portable diagnostic device, a smartphone, and a wireless feedback button. The portable diagnostic device includes a tactile threshold test module, a vibration threshold test module, a thermal threshold test module, infrared skin temperature test module, a microcontroller, a communication module, a Radio Frequency Transceiver and a voltage regulator. The system is energized by a power supply with an adapter or a rechargeable battery pack integrated into the hand held device.

According to one embodiment herein, the portable handheld diagnostic device includes a pointed filament that is pressed on a foot of a subject for performing a tactile threshold test. Further, the device includes a vibratory surface for providing vibrations on the foot of the subject, and two temperature threshold test surfaces for providing cold and hot sensation on the foot of the subject. The temperature threshold test surface includes two Peltier units each equipped with a temperature sensor. The device further includes a contactless infrared temperature sensor module that can measure the skin temperature. The device further includes a power cord with an adapter for connecting the device with an AC input supply. One embodiment of the invention provides a rechargeable battery pack integrated into the hand held device along with the AC power supply.

According to one embodiment herein, the tactile threshold test is performed by a monofilament test that is automated based on strain load cell. The monofilament is a spring loaded filament used to transfer the force applied at its one end to the other end of the monofilament. The tactile threshold test module includes a small piece of monofilament mounted on the surface of a strain load cell. The differential voltage generated in the Wheatstone Bridge of the strain load cell, due to the application of force at the tip of the monofilament, that is in contact with the foot of a subject, is sensed. Further, the differential voltage is amplified using a precision instrumentation amplifier and fed to a microcontroller. Further, the sensed voltage is converted into grams of force by the mobile application and displayed on a user interface of the mobile device.

According to one embodiment herein, the vibration threshold test module includes a combination of vibration motors, a spring and a damping mechanism in a hand held device. In vibration test, the vibration strength is increased gradually until a subject feels the vibration. The vibration motors is driven by a varying duty cycle Pulse Width Modulated Output (PWM) from the microcontroller. The vibration motors are mounted on a spindle with spring and damping mechanism to isolate the vibrations in the application area. The duty cycle is gradually increased at a predetermined rate. Further, a microcontroller is configured to check whether the duty cycle applied to the vibration motor exceeds a pre-determined threshold value. The vibration test is selected from a menu option in the mobile application, and the vibration test surface in the portable diagnostic device is kept at different test points on the feet of the subject. When the vibration is felt at a particular test point, the subject presses wireless feedback button. When the vibration is not felt at a particular test point, the vibration strength is increased until the subject presses the feedback button. Once the subject presses the feedback button, the corresponding value of vibration strength is stored. The results are displayed on a User Interface (UI) of the mobile application. Further, the results are printed and shared with other devices.

According to one embodiment herein, the temperature test module includes two temperature probes, two Peltier modules, heat sinks, a fan, and a pair of temperature sensors. The test involves touching the patient's feet with a gradually heated or cooled temperature probe at various test points and recording the temperature at which the patient senses the hot or cold surface. When the patient feels the heat or cold sensation, at a particular test point, the patient presses the feedback button. The temperature probes are fixed on Peltier modules, which in turn are fixed to a cooling system including a pair of heat sinks and a fan. The cooling system helps to dissipate heat quickly from the Peltier module. The temperature sensors mounted on the Peltier modules help to record the temperature at which the patient presses the feedback button. The Peltier module is controlled using a Pulse Width Modulated Output (PWM) from the microcontroller with the varying duty cycle. The duty cycle is gradually increased at a predetermined rate. The results are displayed on a User Interface (UI) of the mobile application. Further, the results are printed and shared with other devices.

According to one embodiment herein, the contactless skin temperature module includes an light based pointer and an infrared temperature sensor. The test involves measuring the skin temperature at various test points and recording the same. The results are displayed on a User Interface (UI) of the mobile application. Further, the results are printed and shared with other devices.

According to one embodiment herein, a method of performing a combination of tactile test, vibration test, thermal response test, or the contactless skin temperature measurement test using a system for neuropathy detection is disclosed. The method includes selecting a type of test by a user from the plurality of tests displayed on the UI of the smartphone. Once a test is selected, the UI displays a pop-up indicating a point on foot where the measuring device has to be kept. The user places the diagnostic device on a given point on the foot of a subject indicated by the application. The diagnostic device is configured to apply any one of a force or vibration or temperature or contactless skin temperature measurement on the point based on the type of test. The diagnostic device determines the value of force/vibration/temperature applied at the given point or the skin temperature at the given point. The diagnostic device further checks whether the sensation of the force/vibration/temperature test is felt at the given point. Further, the system checks whether the value of applied force/vibration/temperature is greater than the threshold value. When the value of test parameter is less than threshold value, then the diagnostic device checks if the sensation of test is felt at the given point. If a subject feels the sensation, then the subject presses the wireless feedback button. If the value of test parameter is greater than the threshold value, then the system stores the current value of test parameter applied exerted for the given point. The stored results are displayed on the UI of the application. Further, the application provides option of at least one of proceed to another point 'X', Redo the test, and Print results. If proceed to another point 'X' or redo test is selected, then steps starting from checking of sensation is performed again at a point 'X'. Further, the user selects the option of print results displayed in the application. Further, the method includes printing the stored results and sharing with other devices.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
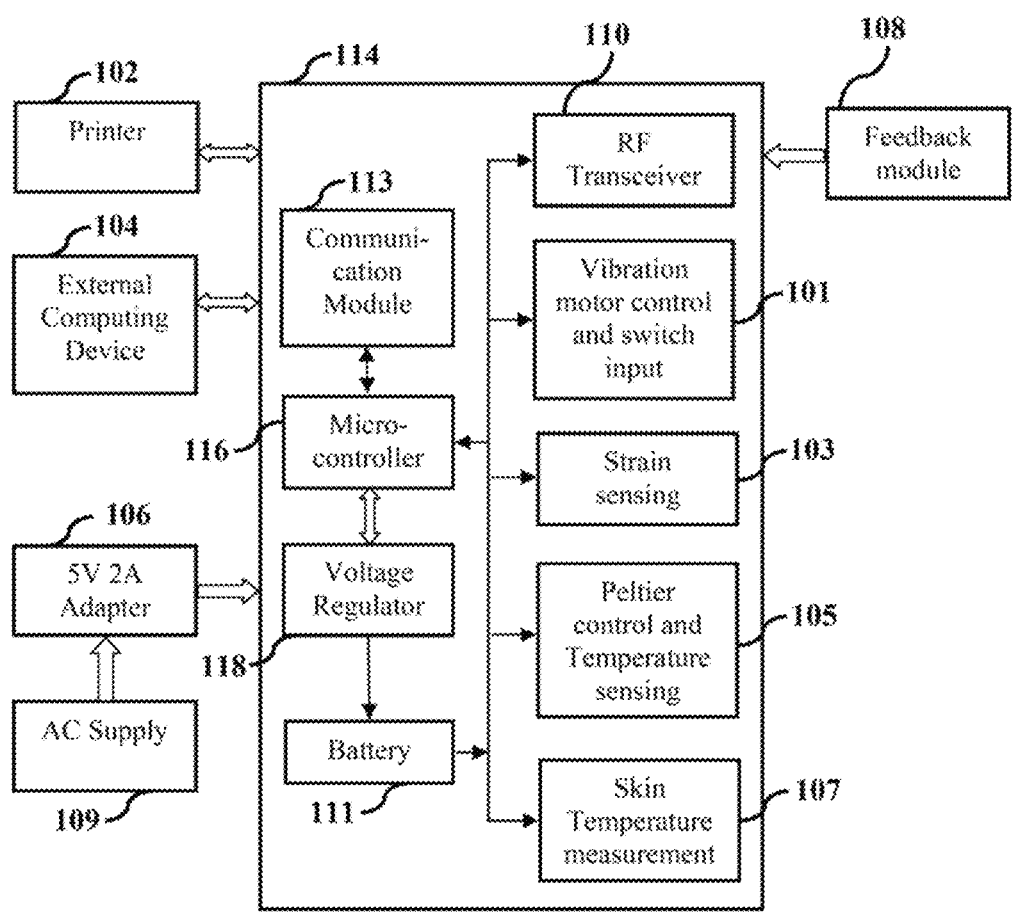
FIG. 1 illustrates a block diagram of a system with a portable handheld diagnostic device for detecting diabetic peripheral neuropathy in a subject, according to one embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS HEREIN

According to one embodiment herein, the system includes a portable diagnostic device, a smartphone, and a wireless feedback button. The portable diagnostic device includes a tactile threshold test module, a vibration threshold test module, a thermal threshold test module, infrared skin temperature test module, a microcontroller, a communication module, a Radio Frequency Transceiver and a voltage regulator. The system is energized by a power supply with an adapter or a rechargeable battery pack integrated into the hand held device.

The various embodiments herein disclose a system with a portable handheld diagnostic device for detecting and/or monitoring nerve impairment or diabetic peripheral neuropathy in a subject. The system provides a multi-parameter diagnostic device, and performs a combination of tactile threshold test, vibration threshold test, thermal threshold test or contactless skin temperature measurement. The system includes a wireless feedback button to record a feedback of the subject. A mobile application is provided on a smartphone to control an operation of the device and display the test results. The application is run to guide a user to perform the test and store or print or transfer test report over a communication network. The usage of the invention is not limited to diagnosis of Diabetic Peripheral Neuropathy, but also to the diagnosis of Fibromyalgia, Complex Regional Pain Syndrome, Lower back pain diagnosis, Erectile Dysfunction, and Large Fiber Impairment Diagnosis. Further, the diagnostic device is applicable for human and veterinary diagnostics. Further, the test points are not limited to the feet and can be on any part of the body.

According to one embodiment herein, the portable handheld diagnostic device includes a pointed filament that is pressed on a foot of a subject for performing a tactile threshold test. Further, the device includes a vibratory surface for providing vibrations on the foot of the subject, and two temperature threshold test surfaces for providing cold and hot sensation on the foot of the subject. The temperature threshold test surface includes two Peltier units each equipped with a temperature sensor. The device further includes a contactless infrared temperature sensor module that can measure the skin temperature. The device further includes a power cord with an adapter for connecting the device with an AC input supply. One embodiment of the invention provides a rechargeable battery pack integrated into the hand held device along with the AC power supply.

According to one embodiment herein, the tactile threshold test is performed by a monofilament test that is automated based on strain load cell. The monofilament is a spring loaded filament used to transfer the force applied at its one end to the other end of the monofilament. The tactile threshold test module includes a small piece of monofilament mounted on the surface of a strain load cell. The differential voltage generated in the Wheatstone Bridge of the strain load cell, due to the application of force at the tip of the monofilament, that is in contact with the foot of a subject, is sensed. Further, the differential voltage is amplified using a precision instrumentation amplifier and fed to a microcontroller. Further, the sensed voltage is converted into grams of force by the mobile application and displayed on a user interface of the mobile device.

According to one embodiment herein, the vibration threshold test module includes a combination of vibration motors, a spring and a damping mechanism in a hand held device. In vibration test, the vibration strength is increased gradually until a subject feels the vibration. The vibration motors is driven by a varying duty cycle Pulse Width Modulated Output (PWM) from the microcontroller. The vibration motors are mounted on a spindle with spring and damping mechanism to isolate the vibrations in the application area. The duty cycle is gradually increased at a predetermined rate. Further, a microcontroller is configured to check whether the duty cycle applied to the vibration motor exceeds a pre-determined threshold value. The vibration test is selected from a menu option in the mobile application, and the vibration test surface in the portable diagnostic device is kept at different test points on the feet of the subject. When the vibration is felt at a particular test point, the subject presses wireless feedback button. When the vibration is not felt at a particular test point, the vibration strength is increased until the subject presses the feedback button. Once the subject presses the feedback button, the corresponding value of vibration strength is stored. The results are displayed on a User Interface (UI) of the mobile application. Further, the results are printed and shared with other devices.

According to one embodiment herein, the temperature test module includes two temperature probes, two Peltier modules, heat sinks, a fan, and a pair of temperature sensors. The test involves touching the patient's feet with a gradually heated or cooled temperature probe at various test points and recording the temperature at which the patient senses the hot or cold surface. When the patient feels the heat or cold sensation, at a particular test point, the patient presses the feedback button. The temperature probes are fixed on Peltier modules, which in turn are fixed to a cooling system including a pair of heat sinks and a fan. The cooling system helps to dissipate heat quickly from the Peltier module. The temperature sensors mounted on the Peltier modules help to record the temperature at which the patient presses the feedback button. The Peltier module is controlled using a Pulse Width Modulated Output (PWM) from the microcontroller with the varying duty cycle. The duty cycle is gradually increased at a predetermined rate. The results are displayed on a User Interface (UI) of the mobile application. Further, the results are printed and shared with other devices.

According to one embodiment herein, the contactless skin temperature module includes an light based pointer and an infrared temperature sensor. The test involves measuring the skin temperature at various test points and recording the same. The results are displayed on a User Interface (UI) of the mobile application. Further, the results are printed and shared with other devices.

According to one embodiment herein, a method of performing a combination of tactile test, vibration test, thermal response test, or the contactless skin temperature measurement test using a system for neuropathy detection is disclosed. The method includes selecting a type of test by a user from the plurality of tests displayed on the UI of the smartphone. Once a test is selected, the UI displays a pop-up indicating a point on foot where the measuring device has to be kept. The user places the diagnostic device on a given point on the foot of a subject indicated by the application. The diagnostic device is configured to apply any one of a force or vibration or temperature or contactless skin temperature measurement on the point based on the type of test. The diagnostic device determines the value of force/vibration/temperature applied at the given point or the skin temperature at the given point. The diagnostic device further checks whether the sensation of the force/vibration/temperature test is felt at the given point. Further, the system checks whether the value of applied force/vibration/temperature is greater than the threshold value. When the value of test parameter is less than threshold value, then the diagnostic device checks if the sensation of test is felt at the given point. If a subject feels the sensation, then the subject presses the wireless feedback button. If the value of test parameter is greater than the threshold value, then the system stores the current value of test parameter applied exerted for the given point. The stored results are displayed on the UI of the application. Further, the application provides option of at least one of proceed to another point 'X', Redo the test, and Print results. If proceed to another point 'X' or redo test is selected, then steps starting from checking of sensation is performed again at a point 'X'. Further, the user selects the option of print results displayed in the application. Further, the method includes printing the stored results and sharing with other devices.

The various embodiments of the present invention disclose a method and a system with a portable handheld diagnostic device for detecting and/or monitoring nerve impairment or diabetic peripheral neuropathy. The present invention provides a multi-parameter diabetic neuropathy-screening device to perform a combination of tactile threshold test, vibration threshold test, thermal threshold test or contactless skin temperature measurement test. The present invention provides a smartphone application that helps a user to operate/control the device, store and share the results. The smartphone application interacts with the hardware modules in the device and guides the user to perform the various tests. Further, the present invention provides a provide neuropathy diagnostic system with a wireless feedback button that enables the subject to respond to various sensation during course of the test. The system allows a health care professional to perform simple and quick, yet accurate test to determine neuropathy in the subject. The device produces instant results that can be printed and further shared with other professionals.

FIG. 1 illustrates a block diagram of a system with a portable handheld diagnostic device for detecting and/or monitoring nerve impairment or diabetic peripheral neuropathy in a subject. The system provides a multi-parameter diagnostic device, and performs a combination of tactile threshold test, vibration threshold test, thermal threshold test, or contactless skin temperature measurement test. The system includes a wireless feedback button to record the subject's feedback. The operation, control of the device and display of test results is done using a smart phone application on a mobile device. The application guides the user to perform the test and store or print or transfer test report over a communication network.

According to one embodiment of the present invention, the system includes a portable diagnostic device 114, a smartphone 104, and a wireless feedback button 108. The portable diagnostic device 114 includes a tactile threshold test module 103, a vibration threshold test module 101, a thermal threshold test module 105, a contactless skin temperature test module 107, a microcontroller 116, a communication module 113, a Radio Frequency Transceiver 110 and a voltage regulator 118. The system is energized by a power supply 106 with an AC power adapter or a rechargeable battery pack 111 that is integrated into the hand held device. The portable diagnostic device wirelessly communicates with the smartphone 104, and the wireless button 108 via wireless communication protocols such as Bluetooth, WI-FI ZigBee and the like.

According to one embodiment of the present invention, the tactile threshold test module includes strain sensing. The tactile threshold test module measures the touch sensation at specific locations on the foot of the subject. The tactile threshold test is performed by a monofilament test that is automated based on strain load cell. The tactile threshold test module includes a small piece of monofilament of any material mounted on the surface of a spring steel piece. The spring steel piece is operatively coupled to a strain gauge and further connected to a Wheatstone bridge. The differential voltage due to the application of force at the tip of the monofilament, when in contact with the foot of a subject is sensed. Further, the differential voltage is amplified using a precision instrumentation amplifier and fed to an analog channel of the microcontroller. Further, the sensed voltage is converted into grams of force by the mobile application and displayed on the mobile device. The working of tactile threshold test module is further illustrated in FIG. 7.

The vibration threshold test module measures the vibration threshold at specific locations on the foot of the subject. The test measures the severity of sensation loss a patient with peripheral neuropathy. The vibration threshold test module includes a vibration motor, a spring and a damper in a hand held device. The smartphone application controls the vibration test. The working of vibration threshold test module is further illustrated in FIG. 8.

The temperature threshold test module measures the temperature threshold for warm and cold sensation of the subject. The temperature test module includes a pair of Peltier modules, heat sinks, a fan, and a pair of temperature sensors. The test involves touching the patient's feet at different test points with a gradually heated or cooled surface and recording the temperature at which the patient senses the hot or cold surface. When the patient feels the heat or cold sensation at a particular test point, the patient presses the feedback button.

Figure 9:
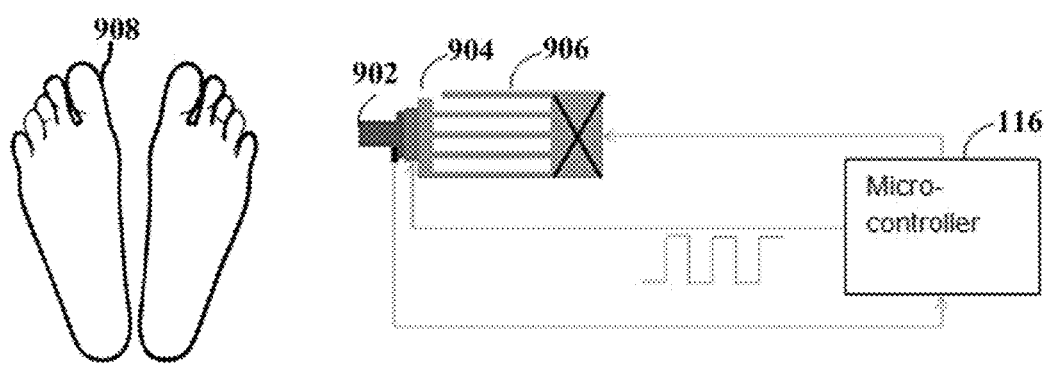
FIG. 9 illustrates a block diagram of the temperature threshold test module included in a portable handheld diagnostic device, according to one embodiment herein.

According to one embodiment, the Peltier module is coupled to the heat sink and the fan as depicted in FIG. 9. The heat sink and the fan forms a cooling system that helps to dissipate heat from the Peltier module. The temperature sensor is mounted on the Peltier module and records the temperature at which the patient presses the feedback button. The mobile application provides an interactive menu guides on the User Interface of the mobile device and further enables the user to perform the temperature threshold test at various points on the foot.

FIG. 2A-2E illustrates a plurality of views of a portable diagnostic device for testing tactile threshold, vibration threshold, thermal threshold and measurement of skin temperature. The handheld portable diagnostic device comprises a Fan 201, a Heat sink 202, a Peltier 203, a Hot temperature test probe tip 204, a Cold temperature test probe tip 205, a Spring loaded tactile test probe 206, Vibration perception test probe 207, a Housing 208, a Keypad 209, a Load cell 210, a Display 211, an Infra-red temperature sensor 212, a LED/laser pointer 213, a first Vibration motor 214, a second Vibration motor 215 and a Spring loaded spindle 216.

Figure 2A:
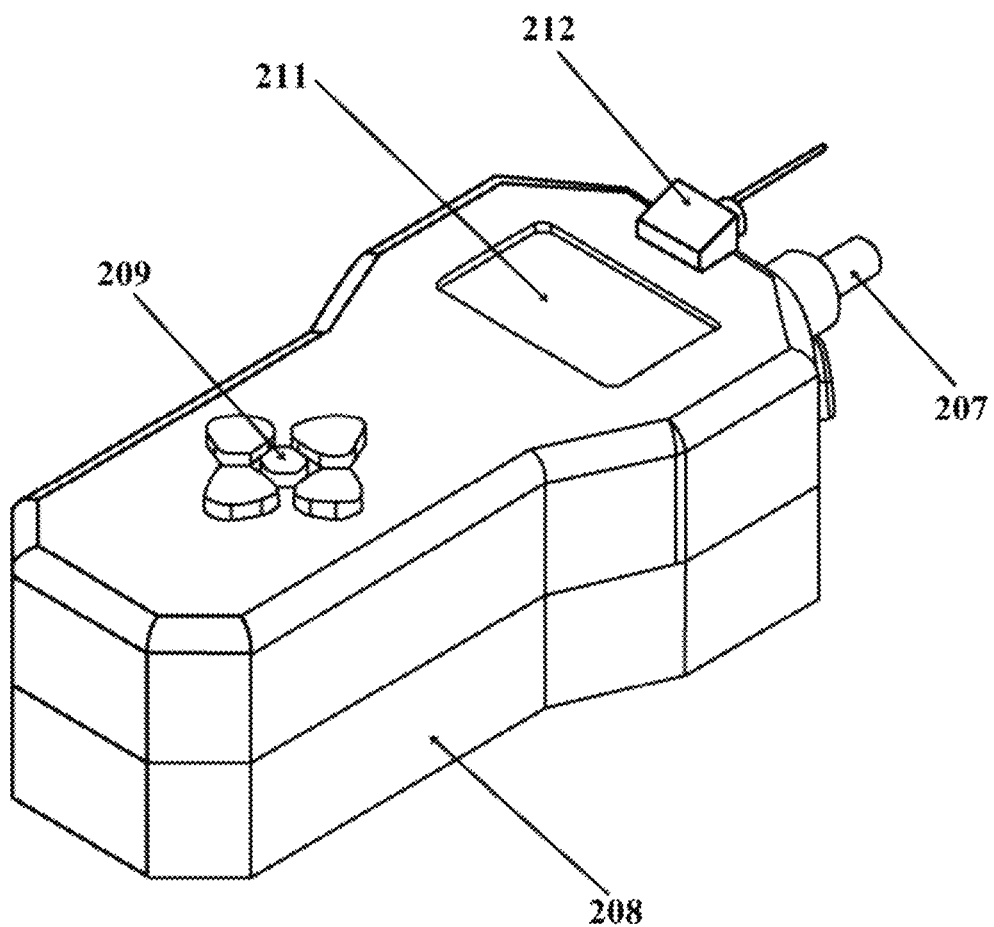
FIG. 2A illustrates a top side perspective view of a portable hand held diagnostic device for testing tactile threshold, vibration threshold, thermal threshold and measurement of skin temperature, according to one embodiment herein.
Figure 2B:
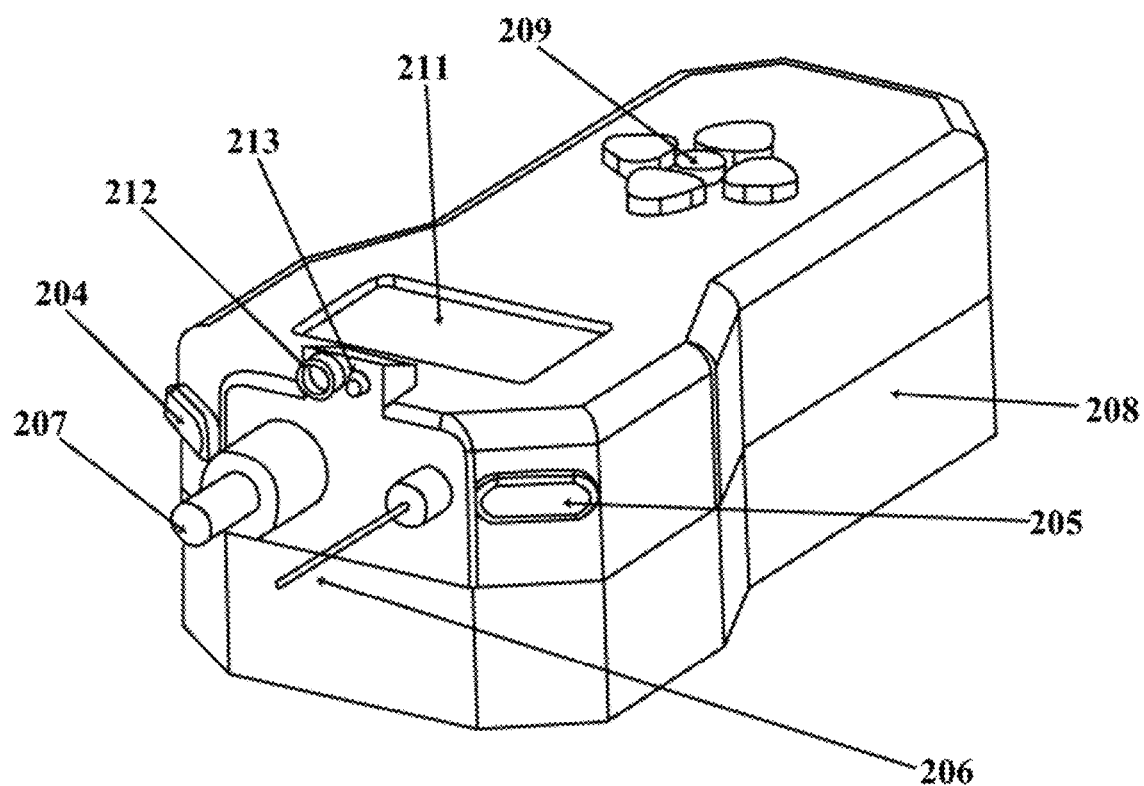
FIG. 2B illustrates a front side perspective view of a portable hand held diagnostic device for testing tactile threshold, vibration threshold, thermal threshold and measurement of skin temperature, according to one embodiment herein.
Figure 2C:
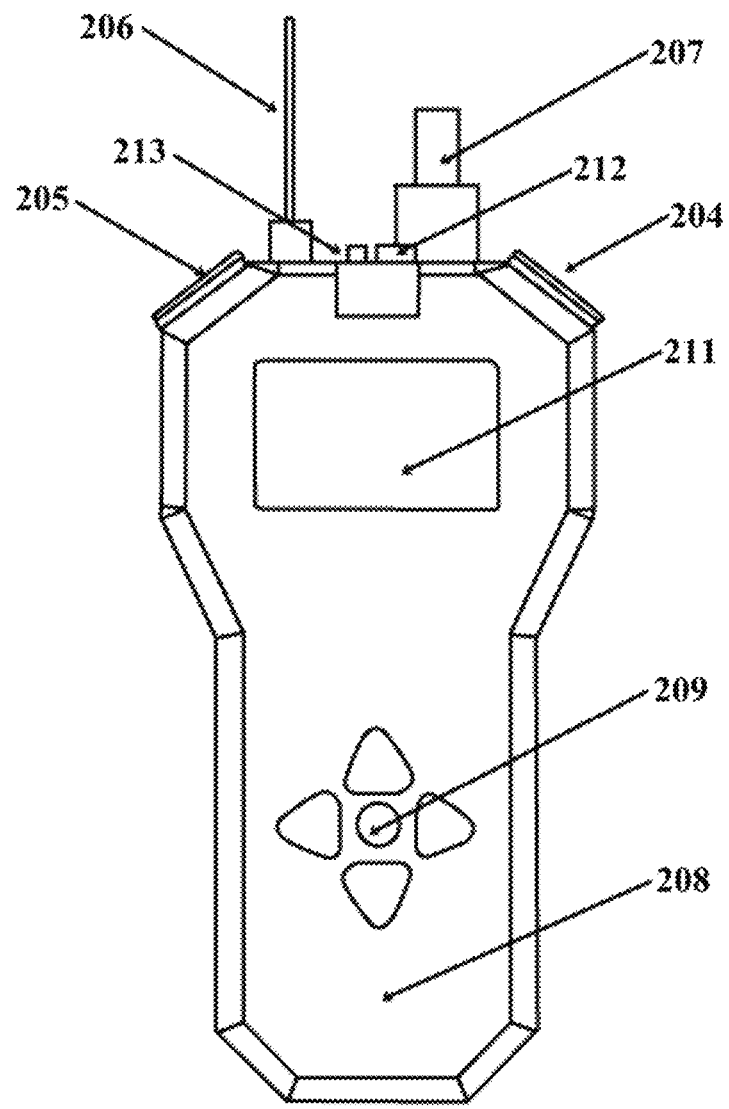
FIG. 2C illustrates top side view of a portable hand held diagnostic device for testing tactile threshold, vibration threshold, thermal threshold and measurement of skin temperature, according to one embodiment herein.
Figure 2D:
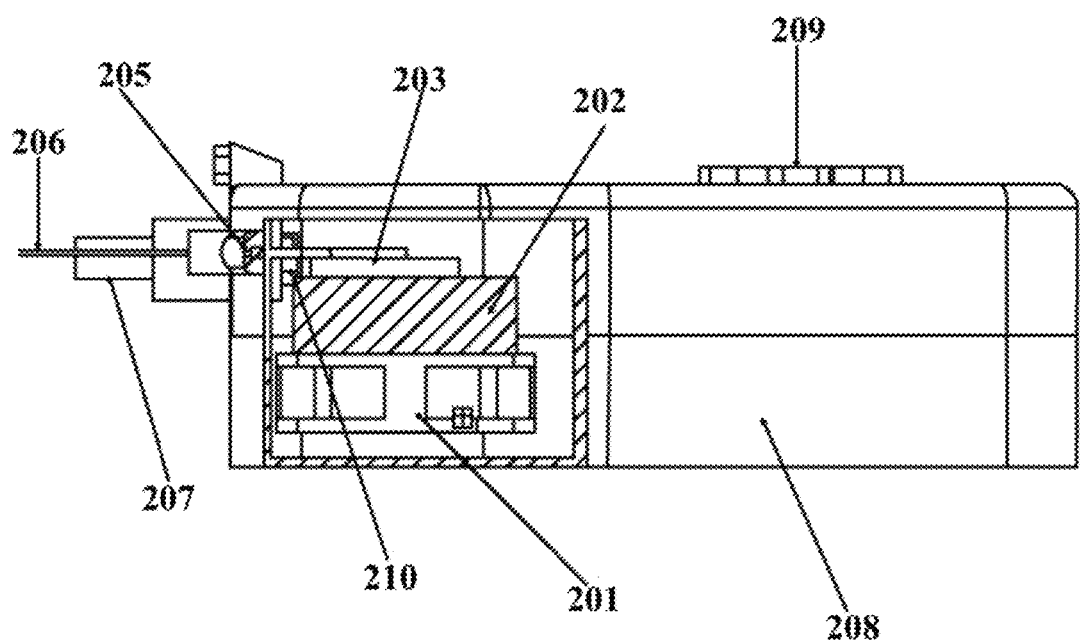
FIG. 2D illustrates a side view of a portable handheld diagnostic device for testing tactile threshold, vibration threshold, thermal threshold and measurement of skin temperature, according to one embodiment herein.
Figure 2E:
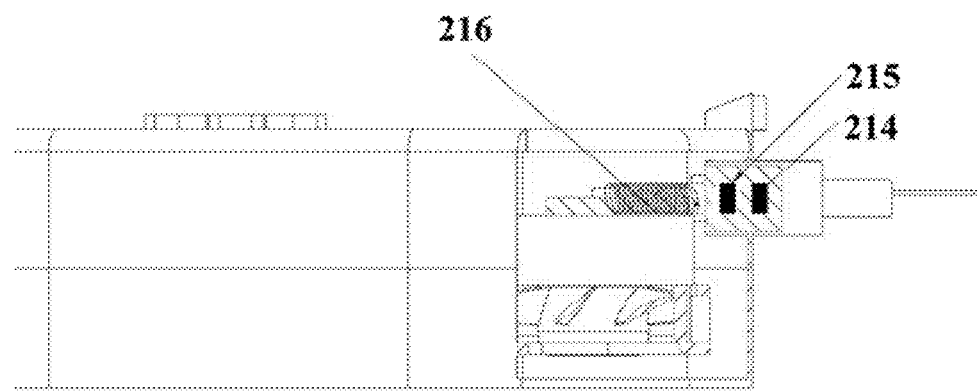
FIG. 2E illustrates a side view of a portable handheld diagnostic device for testing tactile threshold, vibration threshold, thermal threshold and measurement of skin temperature, according to one embodiment herein.

According to one embodiment of the present invention, the vibration perception test module includes a combination of vibration motors 214, 215 which are mounted on a spring loaded spindle 216 and the heat sink 202 as depicted in FIGS. 2D and 2E. The vibration threshold test module measures the vibration threshold at specific locations on the foot of the subject. The test measures the severity of sensation loss a patient with peripheral neuropathy.

According to one embodiment of the present invention, the contactless skin temperature measurement module includes an infra-red temperature sensor 212 and a LED/laser pointer 213 as depicted in FIG. 2B.

Figure 3:
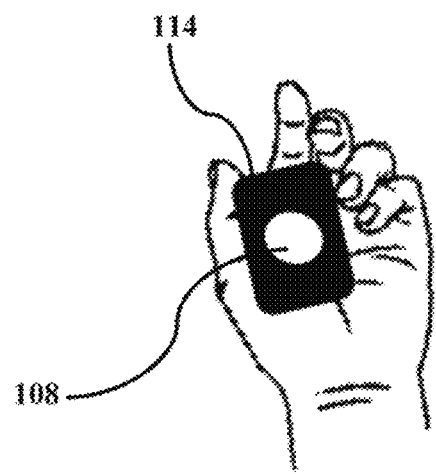
FIG. 3 illustrates a front view of a feedback mechanism of a portable diagnostic device held in a hand of a user, according to one embodiment herein.

FIG. 3 illustrates a feedback mechanism of a portable diagnostic device. The portable diagnostic device 114 comprises a switch 108, which enables the user to trigger feedback information and communicate to the testing and measurement modules. The computing module also records the time at which the feedback information is triggered and enables measurement of the response of the user.

Figure 4:
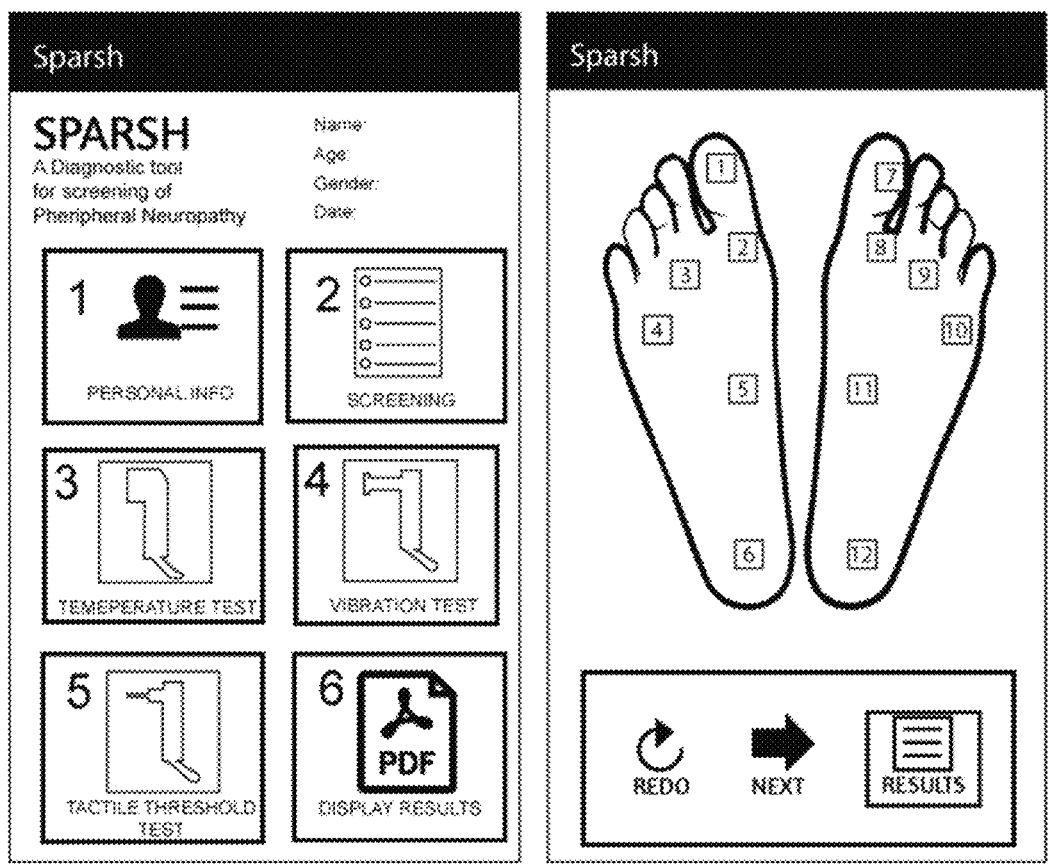
FIG. 4 illustrates a screen shot of a user interface of the mobile application installed in a smartphone for performing/controlling tests related to diagnosing neuropathy in a subject.

FIG. 4 illustrates a user interface of the mobile application installed in a smartphone for performing/controlling tests related to diagnosing neuropathy. The UI displays an interactive menu with a plurality of options such as tactile threshold test, vibration threshold test, temperature threshold test, and print results. According to one embodiment of the present invention, a user selects tactile threshold test, then a pop-up opens up indicating the point of foot where the measuring device has to be kept. Once, the measurement is done, the user can select the option redo test. If not, the user can proceed to print results corresponding to the test.

Figure 5:
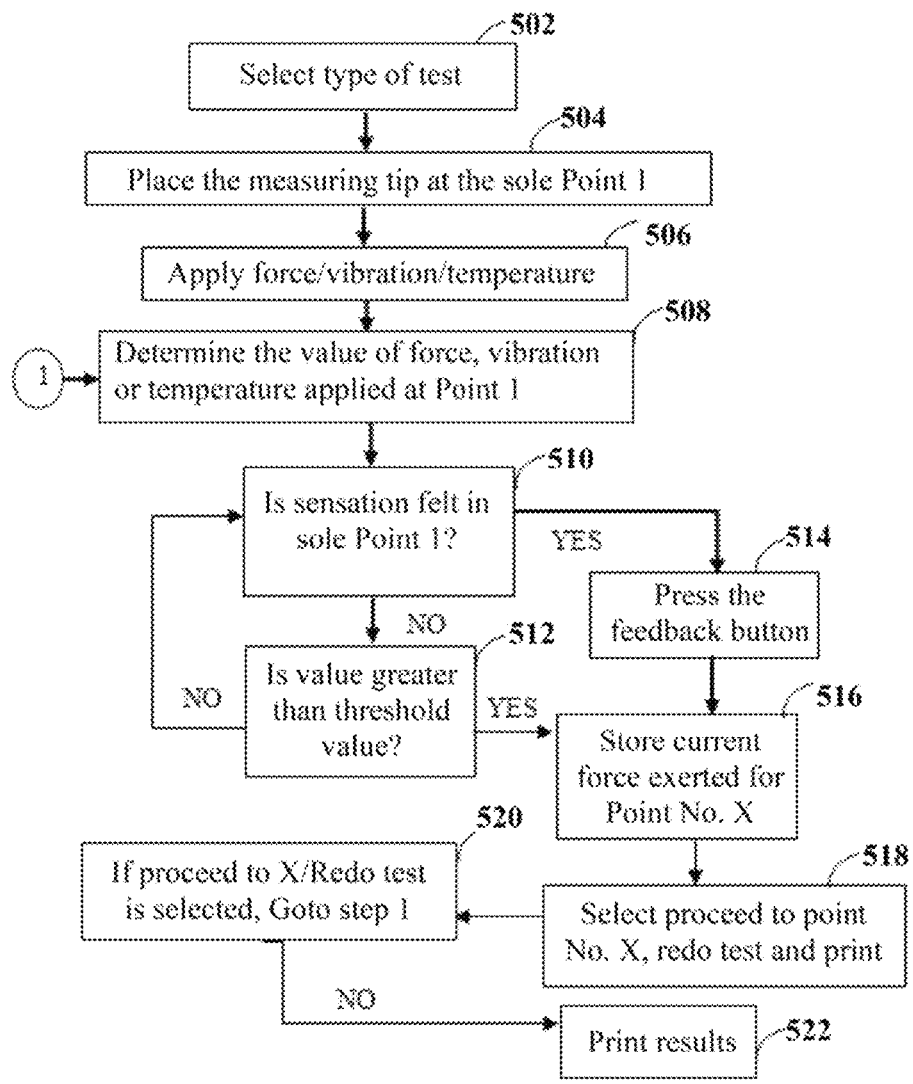
FIG. 5 illustrates a flowchart explaining the process of performing a combination of tactile threshold test, vibration threshold test, or thermal threshold test using a system for neuropathy detection, according to one embodiment herein.

FIG. 5 illustrates a flowchart explaining the method of performing a combination of tactile threshold test, vibration threshold test, or thermal threshold test using a system for neuropathy detection. The system includes a portable diagnostic device, a smartphone, and a wireless feedback button. The portable diagnostic device includes a tactile threshold test module, a vibration threshold test module, and a thermal threshold test module. The smartphone is installed with an application providing a User Interface (UI) displaying an interactive menu with a plurality of options such as Tactile threshold test, vibration threshold test, temperature threshold test, and contactless skin temperature measurement. The application interacts with the hardware modules and guides the user to perform the above mentioned tests. Thus, the smart phone application enables a user to operate and control the various tests.

At step 502, the user can select a type of test from the plurality of tests displayed on the UI of the smartphone. Once a test is selected, the UI displays a pop-up indicating a point on foot where the measuring device has to be kept. At step 504, the user places the diagnostic device on the point '1' on the foot of a subject indicated by the application. At step 506, the diagnostic device applies one of a force or vibration or temperature on the point based on the type of test. At step 508, the diagnostic device determines the value of force/vibration/temperature applied at the point '1'. At step 510, the diagnostic device checks if the sensation of test is felt at the point '1'. If the sensation is not felt, then step 512 is performed. At step 512, the system checks if the value of force/vibration/temperature applied is greater than the threshold value. If the value of test parameter is less than threshold value, then step 510 is performed. If the value of test parameter is greater than the threshold value, then step 516 is performed. At step 514, if a subject feels the sensation, then he/she presses the wireless feedback button. At step 516, the system stores the current value of test parameter applied exerted for point No. '1'. The stored results are displayed on the UI of the application. Further, the application provides option of proceeding to another point 'X', Redo the test, and Print results. At step 520, if proceed to X and redo test is selected, then steps starting from 508 is performed again at a point 'X'. At step 522, the user selects the option of print results displayed in the application. Then the stored results are printed and shared with other devices.

Figure 6A:
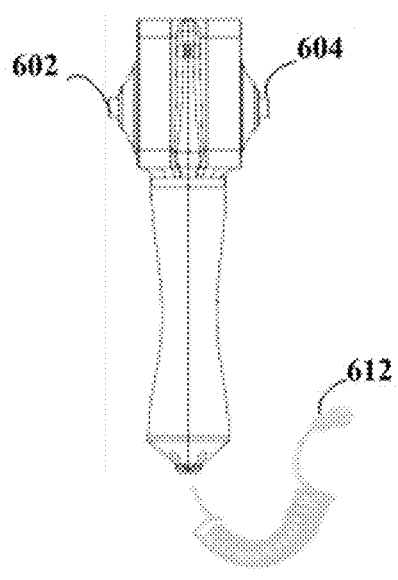
FIG. 6A illustrates a front side view of a portable handheld diagnostic device for performing a combination of tactile test, vibration test, or thermal response test for detecting neuropathy, according to one embodiment herein.
Figure 6B:
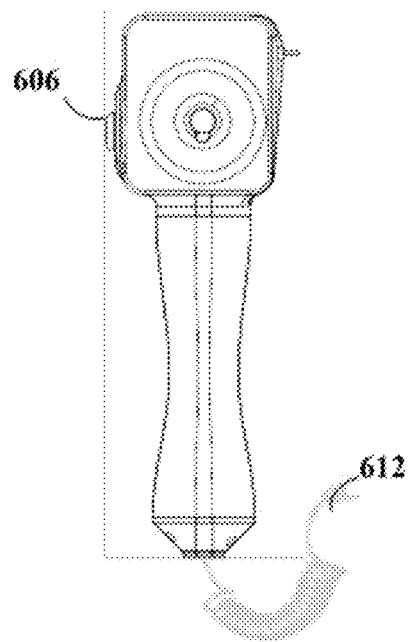
FIG. 6B illustrates a right side view of the portable handheld diagnostic device for performing a combination of tactile test, vibration test, and thermal response test for detecting neuropathy, according to one embodiment herein.
Figure 6C:
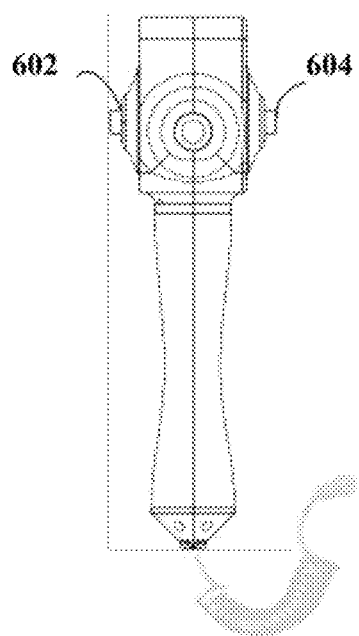
FIG. 6C illustrates a left side view of the portable handheld diagnostic device for performing a combination of tactile test, vibration test, or thermal response test for detecting neuropathy, according to one embodiment herein.
Figure 6D:
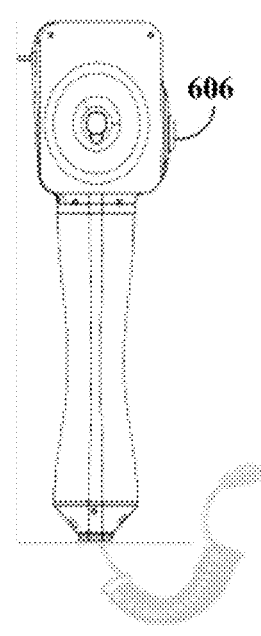
FIG. 6D illustrates a rear side view of the portable handheld diagnostic device for performing a combination of tactile test, vibration test, or thermal response test for detecting neuropathy, according to one embodiment herein.
Figure 6E:
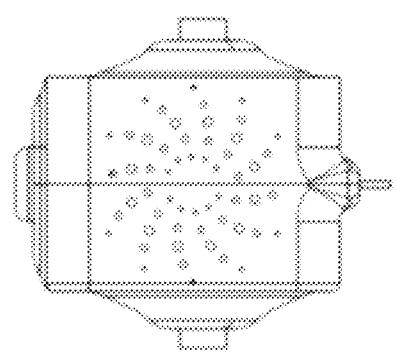
FIG. 6E illustrates a top side view of the portable handheld diagnostic device for performing a combination of tactile test, vibration test, or thermal response test for detecting neuropathy, according to one embodiment herein.
Figure 6F:
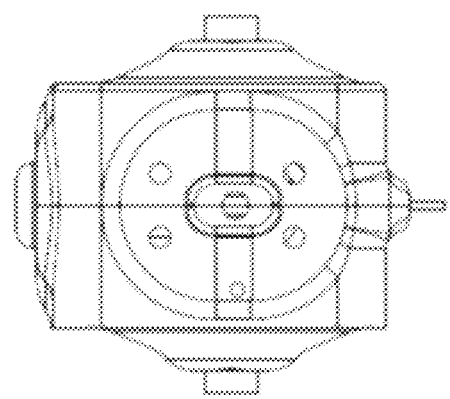
FIG. 6F illustrates a bottom side view of the portable handheld diagnostic device for performing a combination of tactile test, vibration test, or thermal response test for detecting neuropathy, according to one embodiment herein.

FIG. 6A illustrates a front side view of a portable handheld diagnostic device for performing a combination of tactile threshold test, vibration threshold test, or thermal threshold test for detecting neuropathy. FIG. 6B illustrates a right side view of the portable handheld diagnostic device for performing a combination of tactile threshold test, vibration threshold test, or thermal threshold test for detecting neuropathy, according to one embodiment of the present invention. FIG. 6C illustrates a rear side view of the portable handheld diagnostic device for performing a combination of tactile threshold test, vibration threshold test, or thermal threshold test for detecting neuropathy, according to one embodiment of the present invention. FIG. 6D illustrates a rear side view of the portable handheld diagnostic device for performing a combination of tactile test, vibration test, or thermal response test for detecting neuropathy, according to one embodiment of the present invention. FIG. 6E illustrates a top side view of the portable handheld diagnostic device for performing a combination of tactile test, vibration test, or thermal response test for detecting neuropathy, according to one embodiment of the present invention. FIG. 6F illustrates a bottom side view of the portable handheld diagnostic device for performing a combination of tactile test, vibration test, or thermal response test for detecting neuropathy, according to one embodiment of the present invention.

With respect to FIG. 6A to 6F, the portable handheld diagnostic device includes a pointed filament 602 that is applied on a foot of a subject for performing tactile threshold test. Further, the device includes a vibratory surface 604 providing vibrations on the foot of the subject, and a temperature threshold test surface 606 for providing cold or hot sensation on the foot of the subject. The temperature threshold test surface 606 includes two Peltier unit and two temperature sensors. The Peltier units and the temperature sensors work in collaboration for the temperature threshold test to detect hot sensation. Further, the Peltier units and the temperature sensors work in collaboration to detect cold sensation.

Furthermore, the device includes a power cord 612 with an adapter for connecting the device with an AC input supply. One embodiment of the invention can provide a rechargeable battery pack integrated into the hand held device along with the AC power supply.

Figure 7:
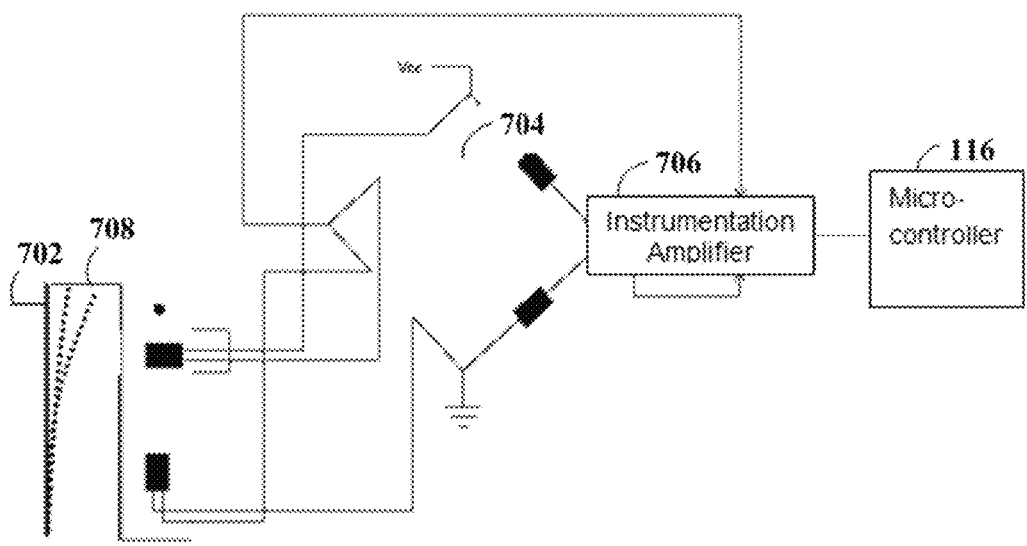
FIG. 7 illustrates a block diagram of the tactile threshold test module included in a portable handheld diagnostic device, according to one embodiment herein.

FIG. 7 illustrates a block diagram of the tactile threshold test module included in a portable handheld diagnostic device, according to one embodiment of the present invention. The tactile threshold test is performed by a monofilament test that is automated based on strain load cell. The tactile threshold test module includes a small piece of monofilament 702 of any material mounted on the surface of a spring steel piece 708. The spring steel piece 708 is operatively coupled to a strain gauge 704 and further connected to a Wheatstone bridge. The differential voltage due to the application of force at the tip of the monofilament, when in contact with the foot of a subject is sensed. Further, the differential voltage is amplified using a precision instrumentation amplifier 706, and fed to an analog channel of the microcontroller 116. Further, the sensed voltage is converted into grams of force by the mobile application and displayed on the mobile device.

Figure 8:
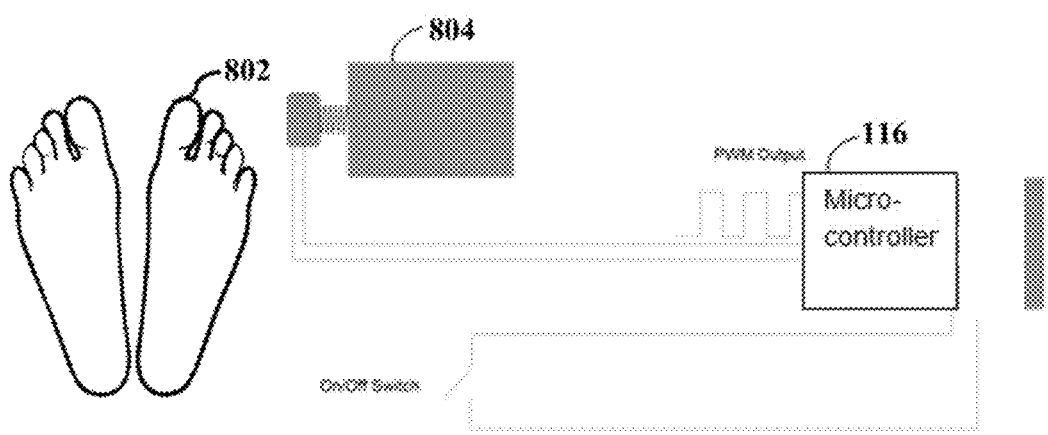
FIG. 8 illustrates a block diagram of the vibration threshold test module included in a portable handheld diagnostic device, according to one embodiment herein.

FIG. 8 illustrates a block diagram of the vibration threshold test module included in a portable handheld diagnostic device, according to one embodiment of the present invention. The test measures the severity of sensation loss in a patient with peripheral neuropathy. The vibration threshold test module includes a vibration motor 802, a spring and a damper 804 in the portable device. In vibration test, the vibration strength is increased gradually until a subject feels the vibration.

According to one embodiment of the present invention, the vibration threshold test module includes a vibration motor driven by a varying duty cycle PWM output from the microcontroller. The vibration motor is mounted on a spring and damper mechanism to isolate the vibrations to the application area. The duty cycle is gradually increased. Further, a microcontroller checks if the voltage supply to the vibration motor exceeds a pre-determined threshold value. The vibration test is selected from a menu in the mobile application, and the vibration test surface in the portable diagnostic device is kept at different test points on the feet of the subject. If the vibration is felt at a particular test point, the subject presses wireless feedback button. If vibration sensation is not felt, the vibration strength is increased until the subject presses the feedback button. Once the subject presses the feedback button, the corresponding value of vibration strength is stored. The results are displayed on a UI of the mobile application. Further, the results can be printed and shared with other devices.

FIG. 9 illustrates a block diagram of the temperature threshold test module included in a portable handheld diagnostic device, according to one embodiment of the present invention. The temperature test module includes a pair of Peltier modules 902, heat sink 904, a fan 906, switch and a pair of temperature sensors 908. The Peltier units and the temperature sensors work in collaboration for the temperature threshold test to detect hot sensation. Further, the Peltier units and the temperature sensors work in collaboration to detect cold sensation. The test involves touching the patient's feet at different test points with a gradually heated or cooled surface and recording the temperature at which the patient senses the hot or cold surface. When the patient feels the heat or cold sensation, the patient presses the feedback button.

According to one embodiment of the present invention, the Peltier module 902 fixed to a cooling system including the heat sink 904 and the fan 906 as shown in the above diagram. The cooling system helps to dissipate heat faster from the Peltier module. The temperature sensors 908 mounted on the Peltier helps to record the temperature at which the patient presses the feedback button.

The Peltier module 902 is controlled using a Pulse Width Modulated Output (PWM) from the microcontroller 116 with the varying duty cycle. The temperature test is selected from an interactive menu in the mobile application, and the temperature test surface in the portable diagnostic device is kept at different test points on the feet of the subject. If a cold or hot sensation is felt at a particular test point, the subject presses wireless feedback button. If cold or hot sensation is not felt at a particular test point, the temperature strength is increased until the subject presses the feedback button. Once the subject presses the feedback button, the corresponding value of temperature is stored. The results are displayed on a UI of the mobile application. Further, the results can be printed and shared with other devices.

The present invention provides a system for detecting and monitoring peripheral neuropathy. The diagnostic device in the present invention allows a health care professional to perform simple and quick, yet accurate test to determine neuropathy in a subject. The diagnostic device produces instant results that can be printed and further shared with other professionals. The test report of the present invention eliminates errors due to interpretation by operator. The diagnostic device is easy to use and inexpensive to manufacture, and is further convenient to carry. The system of the present invention eliminates errors caused by manual methods of the test. Further, the system eliminates inter-measurer variability or increases repeatability of a test.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the disclosure with modifications. However, all such modifications are deemed to be within the scope of the appended claims.

It is also to be understood that the following claims are intended to cover all of the generic and specific features of the embodiments described herein and all the statements of the scope of the embodiments which as a matter of language might be said to fall there between.

What is claimed is:

1. A portable and integrated system for testing tactile threshold, vibration perception, thermal perception and measuring temperature of a skin of a limb, the system comprising:
   a tactile threshold testing module, wherein the tactile threshold testing module comprises a pointed filament pressed on a foot of a person to induce a set of touch sensation at predetermined locations on a limb of the person and record a feedback through a feedback module:
   a vibration perception testing unit module comprising a combination of vibration motors, a spring and a damping mechanism, and wherein the vibration perception testing module is configured to induce a set of vibrations at the predetermined locations on the limb of the person and record feedback through the feedback module;
   a thermal perception testing module, and wherein the thermal perception testing module comprises two Peltier modules, a plurality of temperature sensors and a plurality of temperature probes, wherein the two Peltier modules are bolted to a cooling fin and a fan arrangement, and wherein the thermal perception testing module is configured to induce a set of temperatures at the predetermined locations on the limb of the person and record feedback through the feedback module;
   a skin-temperature measurement module, wherein the skin-temperature measurement module comprises an infra-red thermometer, and wherein the infra-red thermometer is configured to measure a temperature of the skin of the person through a non-contact process, and wherein the skin-temperature measurement module includes a LED pointer, or a laser pointer, for focusing or pointing the infra-red thermometer at an area to be measured on the skin;
   a power control module;
   a computing module; and
   wherein the cooling fin and the fan arrangement is designed to dissipate heat from the Peltier modules, and wherein the plurality of temperature sensors and the plurality of temperature probes are mounted on the Peltier modules, and wherein the plurality of temperature probes are designed to induce a temperature variation, and the plurality of temperature sensors are designed to measure a temperature variation at the predetermined locations on the limb of the person and wherein the temperature variations are within predetermined ranges both above and below the ambient temperature.

2. The system according to claim 1, wherein the tactile threshold testing module further comprises a load cell to accurately measure a force applied by the tactile testing module on the limb of the person, and wherein the load cell is mounted on a rigid frame inside the system and wherein a tactile probe is mounted on the load cell, and wherein a tip of the tactile probe is pressed against the skin of the person, and wherein a force applied by the tactile probe is converted into a corresponding voltage by the load cell, and wherein the generated voltage is amplified with a precision instrumentation amplifier and fed to the computing module, and wherein the sensed voltage is converted to grams of force and wherein the measured information is displayed to the person through a display unit in the computing module.

3. The system according to claim 2, wherein the tactile probe of the tactile testing module includes any one of a spring loaded probe, a conventional monofilament commonly used in manual testing, a tactile probe designed based on a requirement of a physician.

4. The system according to claim 1, wherein the vibration perception testing module comprises a plurality of vibrating elements driven in a plurality of mutually different combinations by a varying duty cycle pulse-width modulator output in the computing module, and wherein the plurality of vibrating elements are mounted on a spring and damper mechanism to isolate vibrations induced in an application area at the predetermined location on the limb of the person.

5. The system according to claim 4, wherein the vibrating elements of the vibration perception testing module is selected from a group consisting of Linear Resonant Actuators, Eccentric Mass Vibration Motors, Piezoelectric motors or a combinations of these.

6. The system according to claim 1, wherein the power control module comprises a power adapter, a battery module and a voltage regulator module, and wherein the voltage regulator is connected to the computing module to provide a regulated power supply.

7. The system according to claim 1, wherein the power control module is configured to enable the working of the system through rechargeable portable batteries and through regulated AC power supply.

8. The system according to claim 1, wherein the power control module is configured to enable wireless charging of the rechargeable portable batteries.

9. The system according to claim 1, wherein the computing module comprises a microcontroller module, a communication module and an external computing device and wherein the microcontroller module and the external computing device are communicatively connected to the communication module.

10. The system according to claim 9, wherein the external computing device is any one of a handheld computing device, a desktop computer, a laptop computer, and wherein the external module is loaded or installed with an application, and wherein the application comprises an interactive menu to enable the user to communicatively interact with the plurality of sensing modules in the system and perform a plurality of tests, and wherein the application is executed on the external computing device to display the results of the plurality of tests, reports and print, out the reports to the use and generate an electronic version of the report in a compliant format.

11. The system according to claim 9, wherein the communication module of the computing module is selected from a group consisting of a Bluetooth module, or a Wi-Fi module or a near field communication module, or a ZigBee module.

12. The system according to claim 1, wherein the feedback module is a portable handheld device, and wherein the feedback unit is connected to the testing and measurement modules through a Radio Frequency (RF) transceiver, and wherein the feedback module is configured to prompt the user to trigger a feedback button provided in the portable handheld device to communicate a feed back to the testing and measurement modules, and wherein the computing module is configured to record a time at which the feedback information is triggered to receive a measurement response of the user.

* * * * *